(12) United States Patent
Sanchez-Cano

(10) Patent No.: US 6,808,616 B2
(45) Date of Patent: Oct. 26, 2004

(54) PROCESS FOR THE PREPARATION OF 5-AMINOSALICYCLIC ACID

(75) Inventor: Gaspar Sanchez-Cano, Alicante (ES)

(73) Assignee: Noveon IP Holdings Corp., Cleveland, OH (US)

( * ) Notice: Subject to any disclaimer, the term of this patent is extended or adjusted under 35 U.S.C. 154(b) by 26 days.

(21) Appl. No.: 10/319,737

(22) Filed: Dec. 13, 2002

(65) Prior Publication Data

US 2003/0098243 A1 May 29, 2003

Related U.S. Application Data

(63) Continuation of application No. PCT/EP01/06619, filed on Jun. 12, 2001.

(30) Foreign Application Priority Data

Jun. 15, 2000 (DE) .......................... 100 29 410

(51) Int. Cl.$^7$ ................................. C25B 3/00
(52) U.S. Cl. .......................... 205/437; 205/435; 205/453
(58) Field of Search .................................. 205/432, 435, 205/437, 431, 453

(56) References Cited

U.S. PATENT DOCUMENTS 1,542,265 A * 6/1925 Norris et al. ................ 562/453
4,670,112 A * 6/1987 Lund ........................... 205/435

FOREIGN PATENT DOCUMENTS

| EP | 0253788 | 1/1988 |
| WO | WO 8603194 | 6/1986 |

* cited by examiner

*Primary Examiner*—Edna Wong
(74) *Attorney, Agent, or Firm*—Thoburn T. Dunlap

(57) ABSTRACT

The present invention relates to a new process for the electrochemical preparation of p-aminophenols, especially 5-aminosalicylic acid. The process can be performed at a low temperature of below 50° C.

10 Claims, No Drawings

PROCESS FOR THE PREPARATION OF 5-AMINOSALICYCLIC ACID

This application is a continuation of PCT application No. PCT/EP01/06619 filed on Jun. 12, 2001.

The present invention relates to a new process for the preparation of p-amino-phenols, especially 5-aminosalicylic acid, by the direct electrochemical reduction of a sulfophenylazophenol derivative. The process is preferably conducted at low temperatures and preferably with the use of a specialized electrode.

p-Aminophenols are technologically important compounds, and especially 5-aminosalicylic acid (5-ASA) of formula

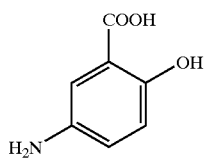

has many applications, for example, in electrophotography, for the preparation of colorants and pigments and, particularly recently, also as an active substance in medicine for the treatment of a number of diseases. Various processes for the preparation of these compounds and especially of 5-ASA have also long been known.

Of particular technological importance is the preparation of 5-ASA by the reduction of 5-azoaromatic derivatives of salicylic acid

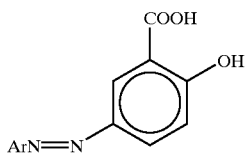

Thus, EP-A-0 253 788 describes the preparation of 5-ASA in the following way, essentially:

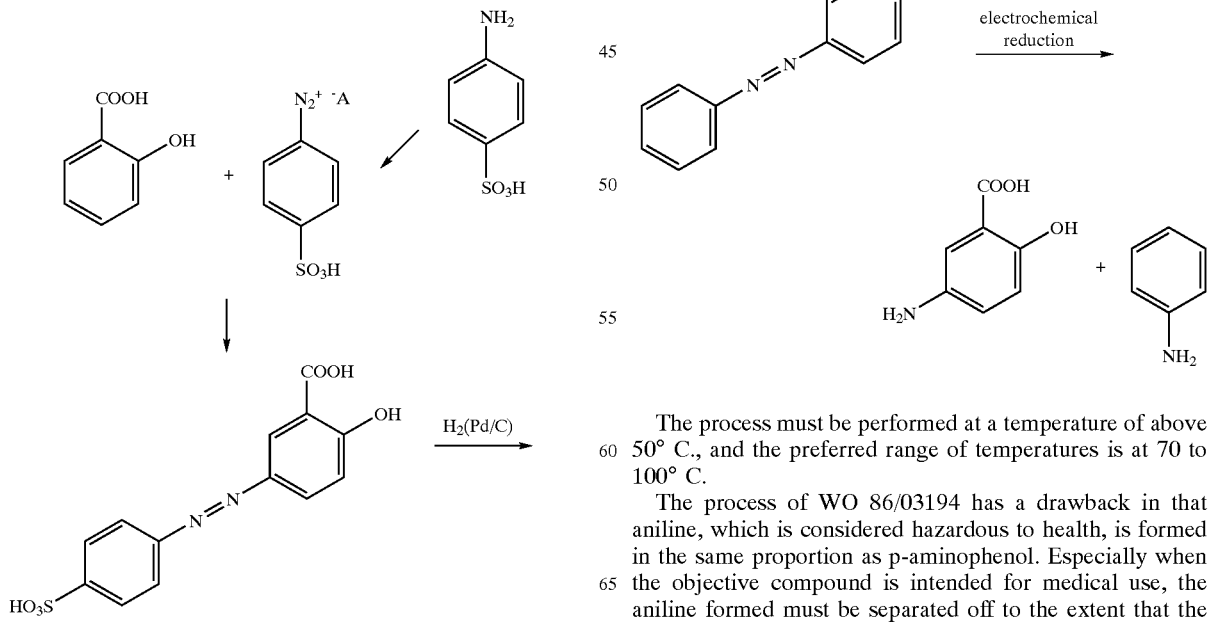

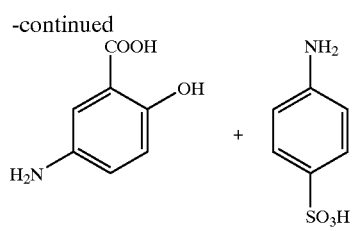

Thus, salicylic acid is first reacted with the diazo salt of sulfanilic acid, and the 5-(para-sulfophenylazo)salicylic acid is then converted to 5-ASA by catalytic hydrogenation. The hydrogenation is done with hydrogen gas on a catalyst at elevated temperatures of above 50° C.

In this reaction, the fact that hydrogen gas must be employed is disadvantageous above all. Although hydrogenations with hydrogen gas are possible on an industrial scale, such processes are undesirable due to a danger of explosion, and extensive safety measures are required, which renders the process more expensive. Also, operation at elevated temperatures is not favorable for economic reasons. Moreover, the final product in the hydrogenation is relatively high in impurities and requires an enhanced expenditure for purification.

WO 86/03194 describes an electrochemical process for the preparation of various p-aminophenols and also of 5-ASA, for example. When interpreted for the production of 5-ASA, the process essentially proceeds according to the following reaction scheme:

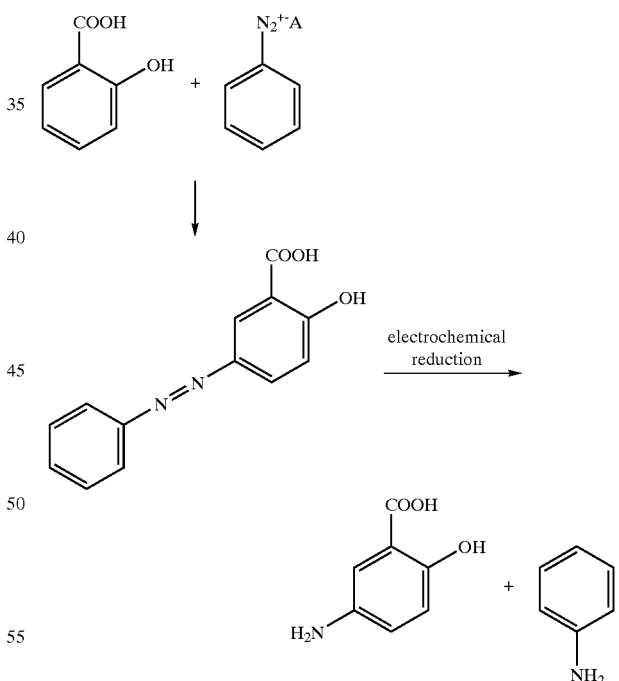

The process must be performed at a temperature of above 50° C., and the preferred range of temperatures is at 70 to 100° C.

The process of WO 86/03194 has a drawback in that aniline, which is considered hazardous to health, is formed in the same proportion as p-aminophenol. Especially when the objective compound is intended for medical use, the aniline formed must be separated off to the extent that the strict legal limit values are met. This is difficult and involves high costs. Also, the process must be conducted at temperatures of clearly above 50° C., which is also undesirable for cost reasons. Further, it is evident from the Examples of the publication that the electrochemical reaction is incomplete, and the electrochemical reaction is followed by a completion of the reaction by the addition of sodium hydrosulfite. The added amounts of sodium hydrosulfite are too high to serve exclusively for the decolorization of the reaction product as stated in the publication. Rather, it is evident that another reasons for this addition is to complete the incompletely proceeded electrochemical reduction by a chemical reduction with sodium hydrosulfite.

Therefore, it has been the object of the present invention to provide a process for the preparation of p-aminophenols, especially 5-ASA, which does not have the drawbacks of the prior art and by which 5-ASA, for example, can be advantageously prepared inexpensively. In particular, the reaction shall also be conducted at low temperatures, since this reduces the formation of by-products.

This object is achieved by the subject matter of the claims.

The invention is based on the surprising finding that sulfonates of general formula

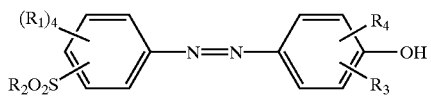

II in which $R_1$ may be hydrogen, a $C_1$–$C_6$ alkyl residue, a hydroxy, sulfonyl or amino group, or a halogen atom, the residue $R_2$ may be $OR_5$ or $NHR_5$, wherein $R_5$ may represent hydrogen or a $C_1$–$C_4$ alkyl group, and the residues $R_1$ may be the same or different, the residues $R_3$ and $R_4$ independently represent hydrogen atoms, $C_1$–$C_4$ alkyl residues, halogen atoms, COOH groups, $SO_3H$ groups or $NO_2$ groups, or their salts, especially their alkali metal salts, can be reduced electro-chemically in a particularly advantageous way, which process can be operated at temperatures of below 50° C. The sulfanil products which are obtained as by-products have not been rated toxic, in contrast to the aniline products obtained in the process of WO 86/03194, and some of them are even employed therapeutically as antibacterial agents. Therefore, separation of the by-product to such a high extent as required when anilines are formed is not necessary in the process according to the invention, depending on the intended use. However, the products formed can always be said to be aniline-free.

According to the invention, in the electrochemical process for the preparation of a compound of formula I

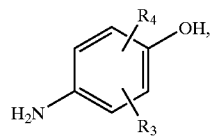

it is preferred to use a compound of formula II in which at least three residues $R_1$ represent a hydrogen atom. Most preferably, all four residues $R_1$ represent a hydrogen atom. Also preferred are compounds of formula II in which the $SO_2R_2$ group is in a para position with respect to the azo group. It is also particularly preferred that the residue $R_2$ represents an OH group. Thus, those compounds are particularly preferred in which all residues $R_1$ represent a hydrogen atom and the residue —$SO_2R_2$ is an —$SO_3H$ group in a p-position with respect to the azo group.

Also particularly preferred are compounds in which the residue $R_3$ represents a hydrogen atom. Also preferred are compounds in which the residue $R_4$ represents a COOH group, which is in turn preferably in an ortho position with respect to the OH group. Salts of these compounds are also preferred.

Thus, as the most preferred compound of formula II, a compound of formula

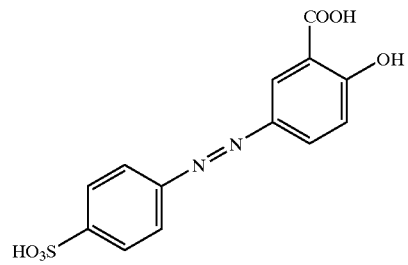

or a salt thereof is employed in the process according to the invention.

The starting compounds of formula II can be prepared by per se known methods, as described in principle, for example, in EP-A-0 253 788. For the preparation of the above mentioned particularly preferred compounds of formula II, the starting compound is sulfanilic acid, while for the preparation of other compounds of formula II, the corresponding derivatives of sulfanilic acid or the corresponding p-aminophenols are employed.

The electrochemical reaction of the compound of formula II can be performed in a per se known manner. Preferably, the electrochemical reaction is performed in a device and with the use of electrodes as are described in EP-A-618 312, included herein by reference. It is also particularly preferred that the electro-chemical reaction is performed in a device and with the use of electrodes as are described in EP-A-778 360, included herein by reference. Unless explicitly stated otherwise in the present specification, the devices and process conditions as described in EP-A-618 312 und EP-A-778 360 are preferred for performing the electrochemical reduction of the compound of formula II to the compound of formula I.

The electrochemical reduction of the compound of formula II is preferably performed in solution, especially in an aqueous solution. Preferably, the pH value of the solution should be greater than 8, more preferably greater than 9.

In a so strongly alkaline solution, the compound of formula II will be present in an ionized form, so that the corresponding salts, especially the alkali metal salts may of course also be employed directly instead of the free acids. The pH value of the solution which is employed for the electrochemical reduction is preferably adjusted by the addition of an alkali metal hydroxide. Optionally, other compounds giving an alkaline reaction may also be employed.

It is particularly preferred to perform the electrochemical reduction according to the invention by using a three-dimensional cathode, especially a three-dimensional carbon cathode, which has a metal collector. Such cathodes are described in EP-A-618 312 and EP-A-778 360 and are also commercially available. A three-dimensional electrode is a porous electrode having a structure, for example, similar to that of glass wool or metal gauze, thus having a large active surface area.

By using such cathodes, the real current density can be kept low due to the large surface area, and a high current efficiency is achieved for the electro-chemical reaction. Although chemical reductants, such as sodium hydrosulfite, are still preferably added at the end of the reaction for decolorization, their amount can be considerably reduced as compared to the process known from WO 86/03194, since completion of the reaction by a chemical reduction with sodium hydrosulfite is no longer necessary.

With the three-dimensional cathode preferred according to the invention, it is also possible to maintain a constant current density throughout the duration of the electrolysis.

In the electrochemical process according to the invention, a usual field separator membrane can be used. More preferably, the separator membrane is a cationic ion-exchanger, which is preferably perfluorinated. Such field separator membranes are commercially available. Again, reference may be additionally made to the field separator membranes disclosed in EP-A-778 360 and EP-A-618 312.

The anodes which can be used are not particularly limited, but there should be used anodes which work satisfactorily even at high pH values. These may be exemplified by nickel anodes. Again, reference may be additionally made to the anodes disclosed in EP-A-778 360 and EP-A-618 312.

According to the invention, the current density is preferably between 500 and 2500 A/m$^2$ and is preferably constant throughout the duration of the reaction. As to the rest, reference may again be made to the current densities disclosed in EP-A-778 360 and EP-A-618 312.

An essential advantage of the process according to the invention is that the electrochemical reduction can be performed at low temperatures. While the process according to WO 86/03194 necessarily requires temperatures of more than 50° C., and in practice even higher than 70° C. is necessary, the process according to the invention is preferably performed at temperatures of below 50° C., more preferably at temperatures of 40° C. or below, especially 30° C. or below.

The reaction times are dependent on the individual parameters of the electro-chemical process. The end of the reaction can be readily established by a skilled person by means of usual methods, such as HPLC. After completion of the electrochemical reduction, the obtained compound of formula I can be isolated by usual chemical methods known in the prior art.

The following Example illustrates the invention.

EXAMPLE 1

Preparation of 5-ASA by the Electrochemical Reduction of 5-(para-sulfophenylazo)salicylic acid

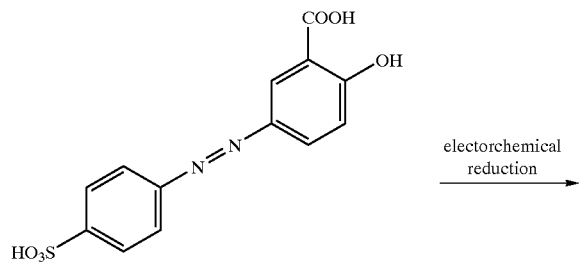

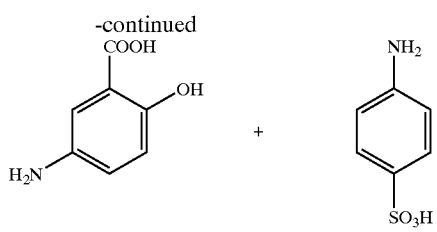

230 kg of 5-(p-sulfophenylazo)salicylic acid (which can be prepared according to "Grundlegende Operationen der Farbenchemie, 8, 5th edition, Vienna 1983, page 150–151") and 85 kg of sodium hydroxide are dissolved in 1500 l of water. The solution is charged into a vessel which is in contact with an electrochemical reactor ("REIM 330 of I. D. Electroquimica S. L., Alicante, Spain). The solution can be passed through the electrochemical reactor at a constant velocity and represents the cathode liquid.

The reactor essentially consists of a commercially available three-dimensional carbon cathode having a high specific surface area and comprising a lead collector. Irrespective of the other parameters of this specific example, a carbon cathode with a metal collector is the most preferred cathode of the present invention. As the metal, there may be used lead, as in the present example, but also cooper, steel or stainless steel. As the anode, an anode is used which can be employed at pH values of 12, for example, an anode which is a available from PERMELEC under the designation of DSA-O$_2$. The electrochemical reactor further contains field separator membrane with a working field of 4 m$^2$. The field separator membrane is cationic and selective in nature. It may be exemplified by the field separator membrane with the designation of NAFION® 450 from Dupont.

As the anode liquid, 900 l of a sodium hydroxide solution is used whose pH value is between 10 and 11. The sodium hydroxide solution is introduced into a vessel which is connected with the electrochemical reactor.

The pH value of the anode liquid is kept constant at a pH value of between 10 and 11 during the process by the controlled addition of 50% sodium hydroxide solution.

During the process, a temperature of from 25° C. to 40° C. is ensured. The cathode liquid and the anode liquid are passed through the electrochemical reactor at a velocity of 5000 l/hour. The power supply is activated at an average current density of 1500 A/m$^2$. The process is conducted for 14 hours. A total charge of 4.4 F per mole of starting compound is circulated, which corresponds to 110% of the theoretical stoichiometric charge.

After 14 hours of conversion, the color of the solution has clearly changed, which indicates that the conversion is complete. The power supply is discontinued, and the solution is transferred into a usual reactor, and 32% aqueous hydrochloric acid solution is added to a pH value of from 3 to 5; 5-ASA precipitates and is filtered off. After drying, 90 kg of 5-ASA having a purity of more than 96% (according to HPLC) is obtained. The 5-ASA is aniline-free.

The anode liquid can be used for another conversion.

What is claimed is:

1. A process for the preparation of p-aminophenols of formula I

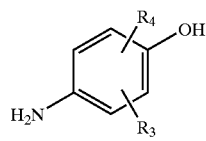

in which $R_3$ and $R_4$ independently represent hydrogen atoms, $C_1$–$C_4$ alkyl groups, halogen atoms, COOH groups, $SO_3H$ groups or $NO_2$ groups, comprising the electrochemical reduction of a compound of formula II

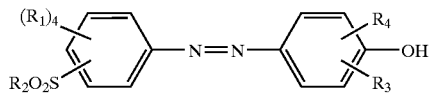

in which $R_1$ independently represents hydrogen, a $C_1$–$C_6$ alkyl group, a hydroxy, sulfonyl or amino group, or a halogen atom, $R_2$ represents $OR_5$ or $NHR_5$, wherein $R_5$ represents hydrogen or a $C_1$–$C_4$ alkyl group, and $R_3$ and $R_4$ are as defined above, or a salt thereof.

2. The process according to claim 1, characterized in that the process is performed in an aqueous solution.

3. The process according to one of the preceding claims, characterized in that the process is performed at a pH value of 7 or greater.

4. The process according to one of the preceding claims, characterized in that $R_1$ in the compound of formula II represents hydrogen.

5. The process according to one of the preceding claims, characterized in that $SO_2R_2$ in the compound of formula II represents an $SO_3H$ group in the para position with respect to the azo group.

6. The process according to one of the preceding claims, characterized in that $R_3$ in the compound of formula II and in the compound of formula I represents a COOH group in an ortho position with respect to the hydroxy group.

7. The process according to claim 6, characterized in that the compound of formula I is represented by the structure:

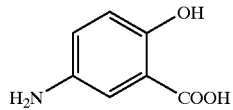

and the compound of formula II is represented by the structure:

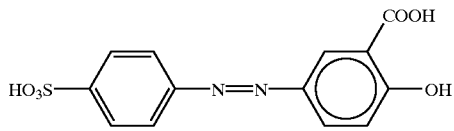

or a salt thereof.

8. The process according to one of the preceding claims, characterized in that the process is performed at a temperature of 50° C. or below.

9. The process according to one of the preceding claims, characterized in that a three-dimensional cathode is used in said electrochemical reduction process.

10. The process according to claim 9, characterized in that the said three-dimensional cathode is a carbon cathode, comprising a metal collector.

* * * * *